(12) United States Patent
Porper et al.

(10) Patent No.: US 6,381,794 B1
(45) Date of Patent: May 7, 2002

(54) ELECTRIC TOOTHBRUSH HAVING DUAL HEADS WITH OSCILLATORY MOVEMENT

(76) Inventors: Robert P. Porper, Mill Pond Offices, 293 Rte. #100 Suite #200, Somers, NY (US) 10589; Robert G. Dickie, 15 Valley Trail, Newmarket, Ontario (CA), L3Y 4V8

( * ) Notice: Subject to any disclaimer, the term of this patent is extended or adjusted under 35 U.S.C. 154(b) by 0 days.

(21) Appl. No.: 09/710,650

(22) Filed: Nov. 13, 2000

Related U.S. Application Data

(63) Continuation-in-part of application No. 09/510,501, filed on Feb. 22, 2000, now abandoned, which is a continuation-in-part of application No. 09/296,631, filed on Apr. 23, 1999, now Pat. No. 6,138,310.

(51) Int. Cl.[7] .............................................. A46B 13/02
(52) U.S. Cl. ...................................... 15/22.1; 15/167.2
(58) Field of Search .................. 15/22.1, 22.2, 15/167.2

(56) References Cited

U.S. PATENT DOCUMENTS

| | | | | |
|---|---|---|---|---|
| 4,131,967 | A | * | 1/1979 | Northemann |
| D259,977 | S | | 7/1981 | Porper |
| 5,027,463 | A | | 7/1991 | Daub |
| 5,259,083 | A | | 11/1993 | Stanbury, Jr. |
| 5,327,607 | A | | 7/1994 | Wagner |
| 5,353,460 | A | | 10/1994 | Bauman |
| 5,359,747 | A | | 11/1994 | Amakasu |
| 5,842,244 | A | * | 12/1998 | Hilfinger |
| 5,842,249 | A | * | 12/1998 | Sato |

FOREIGN PATENT DOCUMENTS

DE          4402366       *  6/1994

OTHER PUBLICATIONS

Amajed, Ibrahim; "A Comparative Study . . ."; The Journal of Clinical Pediatric Dentistry; Fall 1994; vol. 19, No.1.

* cited by examiner

*Primary Examiner*—Randall E. Chin
(74) *Attorney, Agent, or Firm*—Marks & Clerk

(57) ABSTRACT

A brush head portion for an electric toothbrush is adapted to be removably connected to a power handle. The brush head portion comprises a pair of opposed bristle head portions. A longitudinal hollow shaft and terminates at a fixed cover portion which is shaped and dimensioned so as to overlie the pair of opposed bristle head portions, which are mounted on a stem. A longitudinal drive shaft extends through the hollow shaft, and transmits rotational driving force to a crank formed at the outer end of the drive shaft. A drive means is located between each of the bristle head portions and the underside of a respective region of the fixed cover portion, and is mounted on the crank so as to have reciprocating motion imparted thereto as the crank is driven. A wedge is formed on the underside of the fixed cover portion in the region overlying each respective bristle head portion, or on the top surface of each respective block. When a reciprocating motion is imparted to the drive means by the crank, the drive means is moved from side-to-side so as to slide from the top towards the bottom of one of the wedges and from the bottom towards the top of the other of the wedges, so as to impart an oscillatory movement to the pair of opposed bristle head portions.

15 Claims, 8 Drawing Sheets

ELECTRIC TOOTHBRUSH HAVING DUAL HEADS WITH OSCILLATORY MOVEMENT

CROSS-REFERENCE:

This application is a Continuation-In-Part Application of application Ser. No. 09/510,501 filed Feb. 22, 2000, now abandoned, (which, in turn, is a Continuation-In-Part of Ser. No. 09/296,631 filed Apr. 23, 1999, now U.S. Pat. No. 6,138,310), by the same inventors herein.

FIELD OF THE INVENTION

This invention relates to electric toothbrushes, sometimes referred to as mechanical toothbrushes, and is more particularly directed to a portable hand-held, electrically powered, mechanical toothbrush. Specifically, a novel toothbrush having oscillatory movement of a pair of opposed bristle head portions of a dual-head toothbrush is disclosed.

BACKGROUND OF THE INVENTION

The use of manual toothbrushes has, of course, been know for many years. Indeed, the use of mechanical toothbrushes, typically those which are electrically driven, has been known for a number of years. The purpose, in any event, is to clean the teeth, usually with a toothbrush which comprises a plurality of bristles that are used in conjunction with a dentifrice. Very often, the dentifrice is mildly abrasive.

The dental profession has propounded, for many years, a technique known as the "Bass Technique" which, if properly performed, is said to achieve superior results in terms of cleaning one's teeth using a manual toothbrush. Essentially, the Bass Technique requires the user to position a manual toothbrush over a zone of the teeth, and then to use very short stokes so as to more or less vibrate the brush at that zone where the brush has been located. This short-stroke brushing should continue for a period of time—typically, twenty strokes to forty strokes—so as to remove any foreign material from that zone. The brush is then repositioned and typically another twenty to forty short strokes are performed. Because each zone is very small, the Bass Technique can be very time consuming. Moreover, since it is a requirement that the strokes be very short which, in turn, requires excellent muscle control, exercising the Bass Technique can be very tiring.

The theory is that, at the end of any given stroke, the bristles will flex so as to become oriented in such a manner that the ends of the bristles point generally away from the direction of the travel of the bristles across the teeth. However, at the beginning of the next stroke, in the opposite direction, the still-flexed bristles will then be pointed in the direction of the stroke and this may cause the bristle to chisel the foreign material away from the teeth for a moment before the bristle again begins to flex so as to sweep across the surface of the tooth in the zone where it is located.

However, a more efficacious manner for brushing teeth comprises a variation of the Bass Technique, whereby oscillatory movement is imparted to a toothbrush. Of course, such oscillatory movement is not capable of being executed manually.

A purpose of the present invention is to provide an electromechanical toothbrush—that is, an electrically driven, mechanical toothbrush, most typically referred to as an electric toothbrush—which will permit the user to perform a tooth cleaning procedure which improves upon the Bass Technique by imparting oscillatory movement to the toothbrush. In other words, by using the toothbrush of the present invention, the user will be able to locate the toothbrush at a given zone for a short period of time, while executing a plurality of oscillatory motions of the toothbrush to clean the teeth, and then move on to the next zone, thus achieving efficient cleaning of the teeth.

Apart from the removal of leftover food particles and the like, a particular purpose for cleaning the teeth is to remove plaque build-up from the teeth. Typically, when using a manual toothbrush, plaque build-up is removed much more easily from the buccal surfaces of the teeth than from the lingual surfaces of the teeth, with relatively good foreign material removal from the occlusal surfaces of the teeth also being achieved.

One development that has occurred in respect of manual toothbrushes is the provision of twin-headed brushes, whereby the lingual and buccal surfaces of the tooth can be scrubbed using the bristles of the brush at the same time, with the same stroking action of the brush.

As to electric toothbrushes, most electric toothbrushes provide groups of bristles which are located in concentric circles, where the brush head thus provided is rotated or, more usually, it is reciprocally rotated.

Co-pending application Ser. No. 09/296,631 filed Apr. 23, 1999, now U.S. Pat. No. 6,138,310, teaches a toothbrush having twin heads to which a lengthwise reciprocating linear motion is imparted. A Continuation-In-Part application, Ser. No. 09/510,501 filed Feb. 22, 2000, now abandoned, teaches a twin head or dual-head toothbrush which, however, is such that an oscillatory movement is imparted to the pair of opposed bristle head portions of the brush head. Rotational motion of an electric motor is translated by a motion translation means into oscillatory motion of a drive shaft; the longitudinal axis of the brush head is offset from the longitudinal axis of the drive shaft. In a particular embodiment of that toothbrush, a flywheel is driven from a drive shaft, and it in turn drives a pin which is mated to a cam block.

DESCRIPTION OF THE PRIOR ART

Several typical prior art toothbrushes are now described. Among them are several manual toothbrushes which comprise dual, opposed bristle heads. They include PORPER U.S. Design Pat. No. D259,977, issued Jul. 28, 1981, which reveals an early design for a toothbrush having opposed bristle heads.

Another manual toothbrush which is adapted for cleaning multiple sides of the teeth at the same time is shown in WAGNER U.S. Pat. No. 5,327,607, issued Jul. 12, 1994. The toothbrush disclosed in that patent includes further bristles which extend from the spine of the toothbrush so as to contact the occlusal surfaces of the teeth at the same as the buccal and lingual surfaces of the teeth are being contacted while the toothbrush is in use.

A typical prior art electric toothbrush is disclosed in AMAKASU U.S. Pat. No. 5,359,747, issued Nov. 1, 1994. Here, a brush member of the toothbrush is given reciprocal motion in the axial direction while, at the same time, the brush member itself is given a rotary motion. The rotary brush member is rotatably mounted on the end of an attachment connected to a drive shaft, and the reciprocating motion in the axial direction thereof is converted into a rotary motion and transmitted to the rotary brush member by a second transmission mechanism.

Another typical prior art electric toothbrush is disclosed in BAUMAN U.S. Pat. No. 5,353,460, issued Oct. 11, 1994. Here, there is a pair of brush elements with driving mechanism which drives one of the brush elements in oscillation, with linkage between the brush elements so that the second brush element is also driven in oscillation. The two brush elements are preferably oscillated in opposite directions. However, the two brush elements can only contact any one surface of the teeth at a time.

A mechanical toothbrush which is said to effectively replicate the Bass Technique is STANSBURY U.S. Pat. No. 5,259,083, issued Nov. 9, 1993. This power driven mechanical toothbrush comprises a plurality of tuft blocks which are mounted on a cam shaft. The tuft blocks are received in sliding relation in a toothbrush head member, and each tuft block slides linearly in a direction parallel to the longitudinal tuft axis as it is guided by guide rails within the head member between a retracted position and an extended position. The tuft blocks are each driven by the rotatable cam. In use, the tuft bristles are brought into contact with the teeth by the user, before the respective tuft block reaches its extended position, so as to thereby flex the bristles and to cause a lateral motion of the distal end of the bristles along the surface of the teeth. This whipping action of the ends of the bristles causes a wiping action across the surface of the teeth while, at the same time, causing a chiselling action by the ends of the bristles against the teeth, so as to thereby remove foreign material away from the teeth in the region where the bristle chiselling action occurs.

Finally, DAUB U.S. Pat. No. 5,027,463, issued Jul. 2, 1991, teaches a toothbrush which may be used for simultaneously brushing and cleaning the occlusal, lingual, and buccal surfaces of the upper and lower teeth of the user. Here, a bristle support member is provided which anchors bristles which extend from the opposite surfaces thereof. The bristles are arranged so that the central rows of bristles are straight while the intermediate and outer rows of bristles on each of the opposed surfaces of the bristle support member are curved. The straight bristles will engage the occlusal surfaces of the teeth, while the intermediate and outer rows will engage the lingual and buccal surfaces of the teeth.

SUMMARY OF THE INVENTION

In accordance with one aspect of the present invention, there is provided an electric toothbrush which has a power handle and a brush head portion. The power handle portion is adapted to provide a housing for an electric motor and for a driving mechanism which is located at a first end of the power handle portion. The driving mechanism is powered by the electric motor.

The brush head portion is removably attachable at a first end thereof to the first end of the power handle portion. The brush head portion comprises a pair of opposed bristle head portions arranged so as to present two groups of opposed bundles of bristles disposed substantially perpendicularly each to the other, where each of the groups of bundles of bristles on each respective bristle head portion comprises a plurality of rows and a plurality of columnms of bristle bundles.

The brush head portion of the toothbrush of the present invention comprises a longitudinal hollow shaft portion and a fixed cover portion at a second end thereof which is remote from the first end. The cover portion is shaped and dimensioned so as to overlie the pair of opposed bristle head portions.

The pair of opposed bristle head portions is mounted on a stem so as to form a pair of opposed blocks which extend forwardly from the stem in a direction away from the first end of the brush head portion. The stem has a longitudinal axis, and the pair of opposed blocks are disposed at either side of that longitudinal axis.

The longitudinal axis extends through the shaft portion, and has a coupling at a first end which is adapted to receive vocational driving force from the driving mechanism that is mounted in the power handle portion. The longitudinal drive shaft extends longitudinally through the stem along its longitudinal axis, and has a crank which is formed at the second end of the longitudinal drive shaft remote from the first end.

Drive means are located between each pair of opposed blocks and the underside of a respective region of a fixed cover portion which overlies each respective one of the pair of opposed blocks. The drive means is mounted on the crank so as to have reciprocating motion imparted thereto, as the crank is driven from the drive shaft.

A wedge is formed on the underside of the fixed cover portion in the region overlying each respective one of the pair of opposed blocks. Alternatively, a wedge is formed on the top surface of each opposed block.

In either event, when a reciprocating motion is imparted to the drive means by the crank, the drive means is moved from side-to-side so as to slide from the top towards the bottom of one of the wedges, and from the bottom towards the top of the other of the wedges. That, in turn, imparts an oscillatory movement to the pair of opposed bristle head portions of the brush head.

Typically, the wedges are formed on the underside of the respective region of the fixed cover portion, and the drive means may comprise a pair of link arms, each having the driving cam member formed at the end thereof, and extending in a direction parallel to the longitudinal axis of the stem. The top surface of each of the blocks has a channel formed therein so as to receive and retain a respective one of the driving cam members. Thus, each driving cam member is captured in its respective channel between the respective block and wedge, so as to slide in camming relation therebetween. This, in turn, thereby imparts the oscillatory movement of the pair of bristle head portions about the longitudinal axis of the stem portion.

Specifically, when the wedges are formed on the underside of the respective regions of the fixed cover portion, the drive means may comprise a T-shaped shuttle block which has a substantially planar bottom surface and downwardly and outwardly ramped portions in the upper surface thereof. The ramped portions are dimensioned and located so as to interact with the wedges as reciprocating motion is imparted to the shuttle block, so as to cause sliding wedge action between the wedges and the ramped portions of the shuttle block. The planar bottom surface of the shuttle block then reacts against one or the other of the opposed blocks so as to thereby impart the oscillatory movement of the pair of opposed bristle portions about the longitudinal axis of the stem portion.

Typical materials for the brush head portion are ABS; and for the drive shaft and driving means having the cam members formed at each end, they are typically formed from stainless steel.

If a T-shaped shuttle block is used, it is also typically formed from ABS.

Each of the groups of bundles of bristles on each respective bristle head portion comprises a plurality of rows and a plurality of columns of bristle bundles, where the rows of bristle bundles are aligned parallel to the longitudinal axis of the brush head, and the columns of bristles are aligned perpendicular the longitudinal axis of the brush head.

The bristles in each bundle in each row of bristle bundles on each bristle head portion are substantially equal in length. The length of the bristles in the respective row of bristle bundles on each bristle head portion which is closest to the longitudinal axis of the brush head portion is shorter than the length of the bristles in the respective row of bristle bundles on each bristle head portion which is furthest away from the longitudinal axis of the brush head portion. Moreover, the lengths of the bristles in each respective row of bristle bundles on each bristle head portion are progressively longer in each row of bristle bundles which is further away from the longitudinal axis of the brush head portion than an adjacent row of bristle bundles which is closer to the longitudinal axis of the brush head portion.

Typically, the amount of oscillatory motion by the opposed bristle head portions of the brush head portion about the longitudinal axis of the stem is in the range of 3° to 7°. It is found that motion in the range of 4° to 5° is particularly effective and gives a good mouth feel.

The rate of oscillatory movement of the opposed bristle head portions of the brush head about the longitudinal axis of the stem is typically in the range of 4,000 to 6,000 oscillations per minute.

A purpose of the present invention is to provide such an electric toothbrush as described above, which can be used to effectively impart the improved version of the Bass Technique to the toothbrush heads and, thereby, to achieve better tooth cleaning results.

Finally, a purpose of the present invention is to bring an electric toothbrush to the market which can be used for very effective cleaning of the teeth, but which can be brought to the market at relatively low cost compared with many of the prior art electric toothbrushes, due to the relatively uncomplicated structure of the electric toothbrush hereof.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following discussion.

In a paper published in the *Journal of Clinical Paediatric Dentistry*, Vol. 19, No. 1, Fall 1994, ALMAJED describes the superior results obtained by thirty patients ranging in age between 6.6 and 18 years of age, using a double-headed toothbrush, compared with an ordinary manual toothbrush, with and without dentifrice. The double-headed toothbrush is identified with the trade mark TWINBRUSH™, provided by Prevention Health Products, Inc. of Somers, N.Y., U.S.A., and being that which is identified in Porper U.S. Design Pat. No. D259,977, noted above. The results of the tests were such that, even with manual manipulation of the double-headed toothbrush, it was significantly more effective in removing plaque than the single-headed toothbrush. The technique used by the patients is identified as being a modified Bass Technique. The results obtained were statistically significant.

As noted above, a feature of the present invention is essentially to provide a double-headed brush head which effectively replicates that which is shown in the Porper design patent, but with a modified arrangement of rows and columns of bunches of bristles in a preferred embodiment and, in any event, arranged in such a manner so as to be mechanically driven as the brush head portion of an electric toothbrush.

Figure 2:
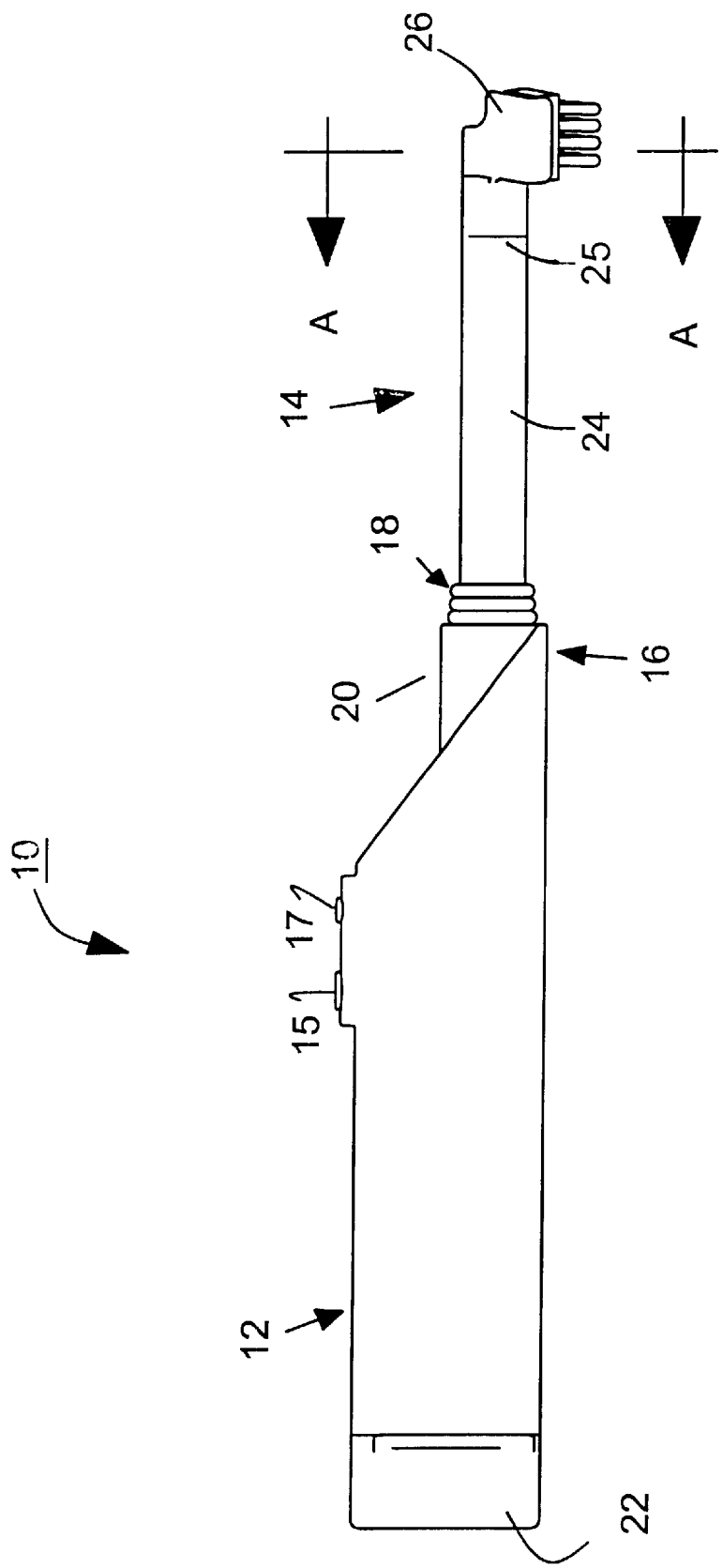
FIG. 2 is a side elevation of a typical electric toothbrush in keeping with the present invention.

The principal elements of an electric toothbrush 10, in keeping with the present invention, are shown in FIG. 2. Here, a power handle 12 and a brush head portion 14 are shown. Typically, the power handle portion 12 provides a housing for an electric motor (not shown), and for a driving mechanism (not shown) which is located at the first end 16 of the power handle portion 12. The driving mechanism is powered by the electric motor, and operation of the toothbrush comes as a consequence of manipulation of "on" and "off" buttons 15, 17. In keeping with the general practice surrounding electric toothbrushes as they are generally found in the market, the brush head portion 14 is removably attachable at a first end 18 thereof, to a socket 20 formed in the power handle portion 12.

Typically, the electric motor is a direct current motor. Even more typically, the direct current motor is powered by a battery (not shown), which is usually a rechargeable battery, and which is stored in the power handle portion 12. Access to the battery, or alternatively to an appropriate electric power transfer arrangement, is formed in the end cap 22. Of course, the electric motor might also be an alternating current motor. Still further, it is possible that a battery might be replaced by a power supply circuit which provides a low voltage direct current power to the electric motor, in either case permitting the electric toothbrush to be plugged directly into a suitable receptacle. All of these matters are outside the scope of the present invention.

Figure 4A:
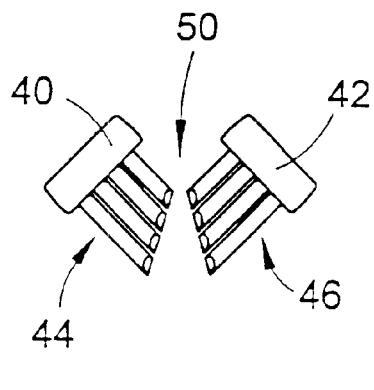
FIG. 4A, 4B, 5, and 6 are end views of the brush head portion of the toothbrush, and of the brush head portion of the toothbrush being in contact with a typical tooth at the rear of the mouth, and in contact with a typical tooth at the front of the mouth, respectively.

Before a detailed description of the mechanism of the present invention is provided, a discussion of the brush head which comprises a pair of opposed bristle heads will first be made, with reference to FIGS. 4, 7, and 8.

The brush head portion 14 comprises a pair of opposed bristle head portions 40 and 42. The bristle head portions 40 and 42 are arranged so as to present two groups of opposed bundles of bristles, indicated at 44 and 46; and the groups of opposed bundles of bristles 44 and 46 are disposed substantially perpendicularly each to the other as shown particularly in FIG. 4A and FIG. 4B.

Figure 4B:
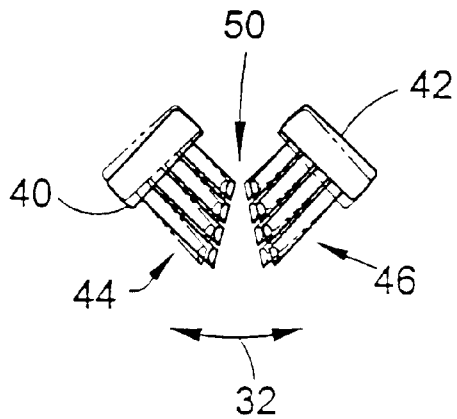

Obviously, FIG. 4B shows the effect of the oscillatory motion of the bristle head portions 40 and 42. One position of those heads is shown in dotted line in FIG. 4B.

Figure 7B:
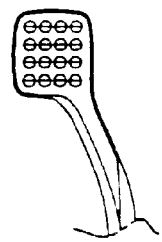
Figure 8A:
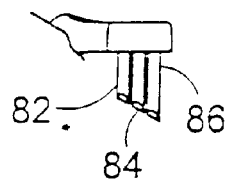
Figure 8B:
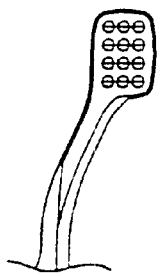

Each of he groups of bundles of bristles on each of the respective bristle head portions 40 and 42 comprises a plurality of rows and a plurality of columns of bristle bundles. For example, FIG. 7B shows four rows and four columns of bristle bundles, whereas FIG. 8B shows three rows and four columns of bristle bundles. The rows of bristle bundles are aligned parallel to the longitudinal axis 34 of the, stem 28 on which they are mounted, and the columns of bristle bundles are aligned perpendicular to the longitudinal axis 34 of the stem 28.

Figure 7A:
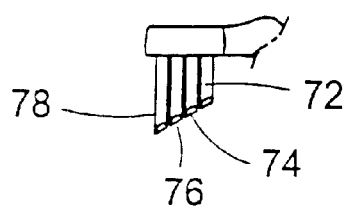
FIGS. 7A, 7B, 7C, and 8A, 8B, and 8C are end, plan, and elevational views, respectively, of two typical configurations of the bristle head portion of a toothbrush in keeping with the present invention.
Figure 7C:
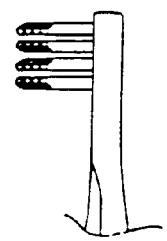
Figure 8C:
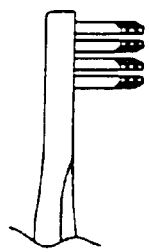

Moreover, it is seen in each of FIGS. 4A, 4B, 7A, and 8A, in particular, that the bristles in each bundle in each row of bristle bundles on each bristle head portion 40 or 42 are substantially equal in length. Still further, it is evident from an inspection of the Figures of drawings, particularly FIGS. 4A, 4B, 7A, and 8A, that the length of the bristles in the respective row of bristle bundles on each of the bristle head portions 40 and 42 which is closest to the longitudinal axis of the brush head portion 14, is shorter than the length of the bristles in the respective row of bristles bundles on each bristle head portion 40 and 42 which is furthest away from the longitudinal axis of the brush head portion 14. Thus, for example, the length of the bristle bundles 72 shown in FIG. 7A is shorter than the length of each of the bristle bundles 78. The same conditions apply with respect to bristle bundles 82 and 86 shown in FIG. 8A.

Still further, the lengths of the bristles in each of the intervening rows of bristle bundles on each bristle head portion are progressively longer in each row of bristle bundles which is further away from the longitudinal axis of the brush head portion than an adjacent row of bristle bundles which is closer to the longitudinal axis of the brush head portion. Thus, the length of the bristle bundles 72 is shorter than the length of the bristle bundles 74 which, in turn, is shorter than the length of the bristle bundles 76, which is shorter again than the length of the bristle bundles 78, all as seen in FIG. 7A. Likewise, the length of the bristle bundles 84, shown in FIG. 8A, is intermediate to the lengths of the bristle bundles 82 and 86.

Typically, the longest bristles 78 or 86 will range in length from about 0.375 inch up to about 0.45 inch, although those dimensions are exemplary only. Also, as typical examples, the length of a bristle head portion having four columns of bristle bundles may be slightly less than one-half inch; whereas the width of a bristle head portion having four row of bristle bundles, as shown in FIG. 7B, might be in the range of 0.45 inch, while the width of a bristle head portion having only three rows of bristle bundles, such as that shown in FIG. 8B, may be in the range of 0.365 inch.

Figure 1:
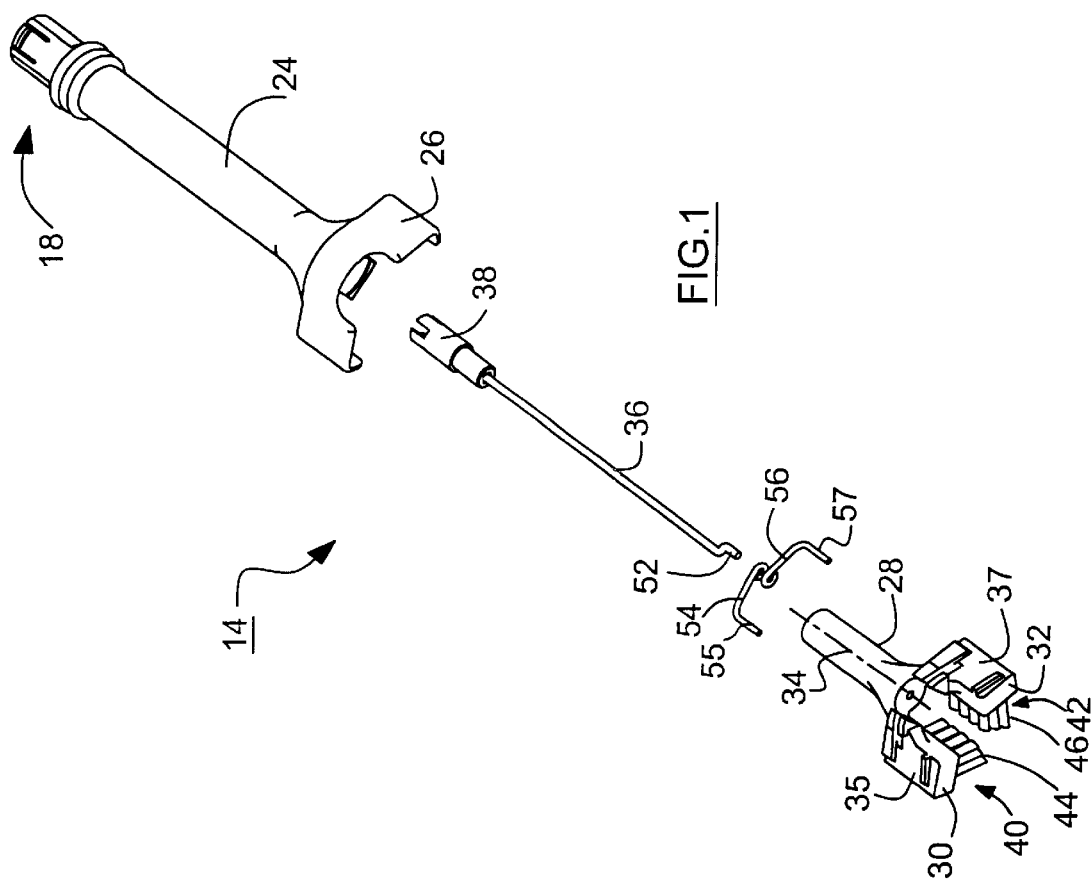
FIG. 1 is a perspective exploded view of the brush head portion of an electric toothbrush in keeping with the present invention.

Referring now to FIGS. 1 and 2, it will be noted that the brush head portion 14 further comprises a longitudinal hollow shaft portion 24 and a fixed cover portion 26. The fixed cover portion 26 is at a second end of the hollow shaft portion 24 remote from the first end 18. It is evident from each of FIGS. 1 and 2, and will become particularly evident from FIGS. 9 through 11, that the fixed cover portion 26 is shaped and dimensioned-soas to overlie the pair of opposed bristle head portions 40, 42.

The bristle head portions 40, 42 are mounted on a stem 28, so as to form a pair of opposed blocks 30, 32, which extend forwardly from the stem 28 in a direction away from the first end 18 of the brush head portion 14. The stem has a longitudinal axis 34; and it will be seen particularly from FIGS. 1 and 9 through 1 that the blocks 30, 32 are disposed at each side of the longitudinal axis 34.

There is a longitudinal drive shaft 36 which extends through the hollow shaft portion 24, and it has a coupling 38 at its first end, which is adapted to receive rotational driving force from the driving mechanism located in the power handle portion 12. Such coupling is conventional.

When the brush head portion 14 is assembled, the longitudinal drive shaft 36 extends longitudinally through the stem 28 along the longitudinal axis 34. The longitudinal drive shaft 36 has a crank 52 formed at its second end, which is remote from the first end when the coupling 38 is located.

A drive means which may comprise a pair of link arms 54, 56, or a shuttle block 90 (see FIG. 3), is located between each pair of opposed blocks 30, 32 and the underside of a respective region of the fixed cover portion 26 which overlies each respective one of the pair of opposed blocks, 30, 32. This arrangement is described in greater detail hereafter, particularly with reference to FIGS. 9 through 11. As will be seen hereafter, the drive means 54, 56, or 90, is mounted on the crank 52 so as to have a reciprocating motion imparted thereto as the crank 52 is driven from the drive shaft 36.

A pair of wedges are employed so as to move the drive means from side-to-side. The present description is in respect of a pair of wedges 100, 102, which are formed on the underside of the fixed cover portion 26 in the region overlying each respective one of the pair of opposed blocks 30 and 32. It will be noted hereafter that the pair of wedges could also be placed on the top surface of each of the blocks 30 and 32, to achieve the same effect.

When a reciprocating motion is imparted to the drive means 54, 56 or 90, particularly as described hereafter, the drive means will be moved from side-to-side so as to slide from the top towards the bottom of one of the wedges and from the bottom towards the top of the other of the wedges. Thus, an oscillatory movement will be imparted to the opposed bristle head portions 40, 42, as will be described particularly with reference to FIGS. 9 through 11.

Turning now to FIG. 1 and FIGS. 9 through 11, a drive means which comprises the pair of link arms 54, 56 is shown, and each has a driving cam member 55, 57 respectively, formed one at each end. Each of the driving cam members 55, 57 extends in a direction which is parallel to the longitudinal axis 34 of the stem 28.

Also, the top surface of each of the blocks 30, 32 has a channel 35, 37 formed therein, whose purpose it is to receive and retain the respective one of the driving cam members 55, 57. When each cam member 55, 57 is captured in its respective channel 35, 37 between a respective block 30, 32 and a respective wedge 100, 102, it will be evident from FIGS. 9 through 11 that the driving cam members 55, 57 slide in camming relation between the respective blocks 30, 32 and wedges 100, 102, so as to impart the oscillatory movement.

Figure 9:
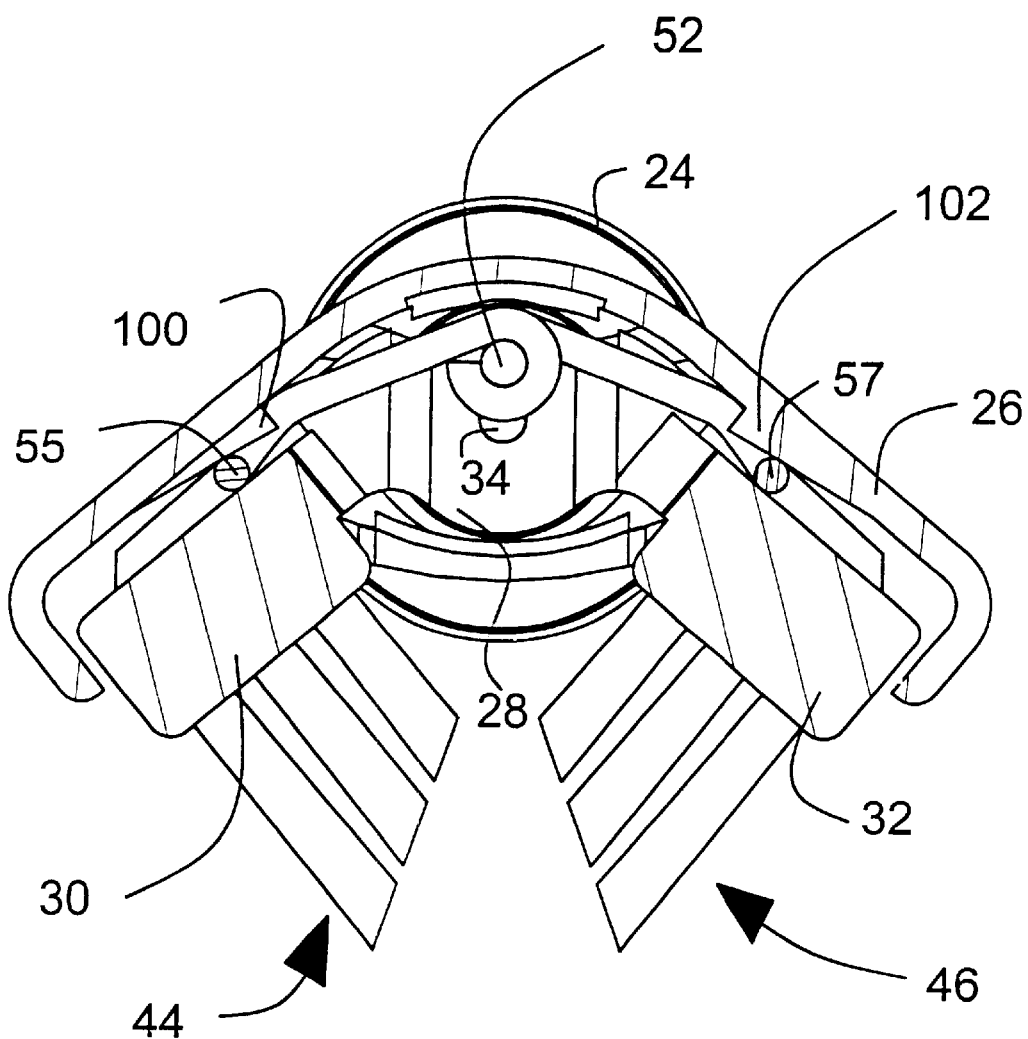
FIG. 9 is a cross-sectional view looking the direction of arrows A—A in FIG. 2, with the blocks of the bristle head portion of the toothbrush being in a first, neutral, position.
Figure 10:
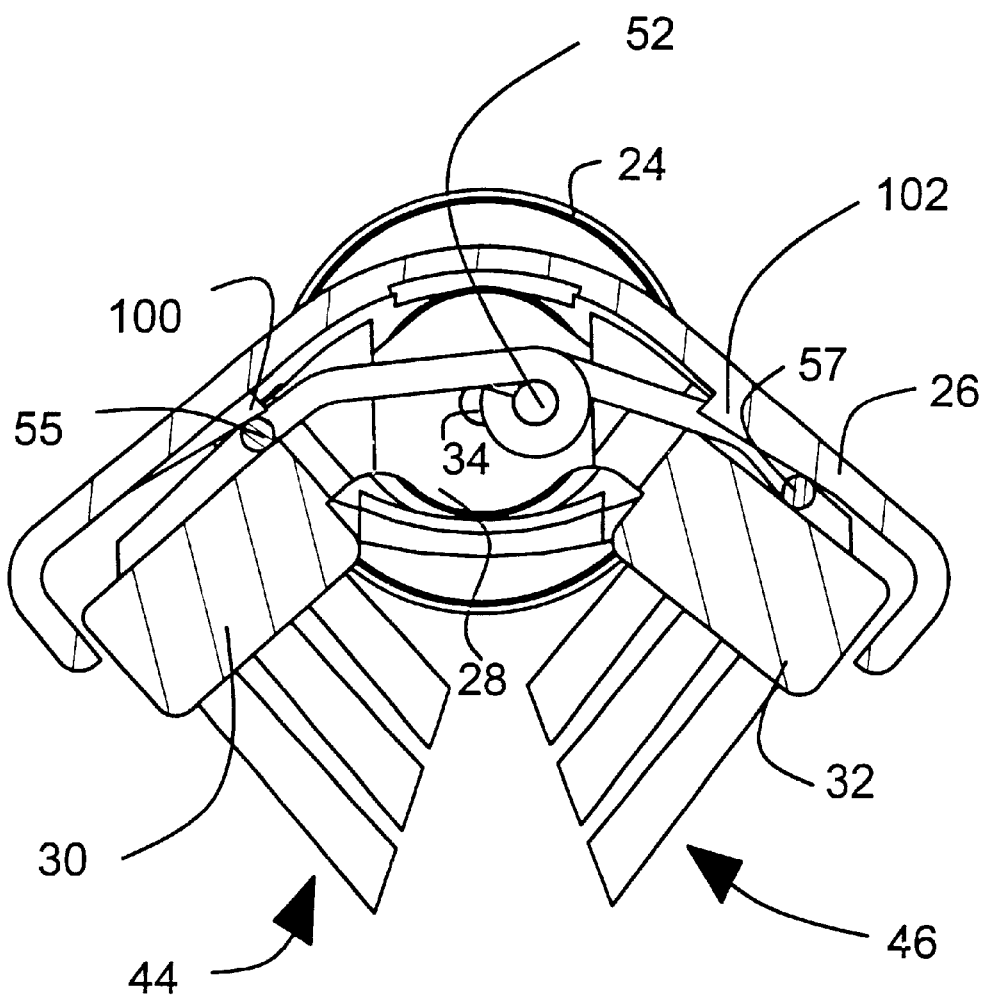
FIG. 10 is view similar to FIG. 9, with the blocks having been rotated to their counter-clockwise limit.
Figure 11:
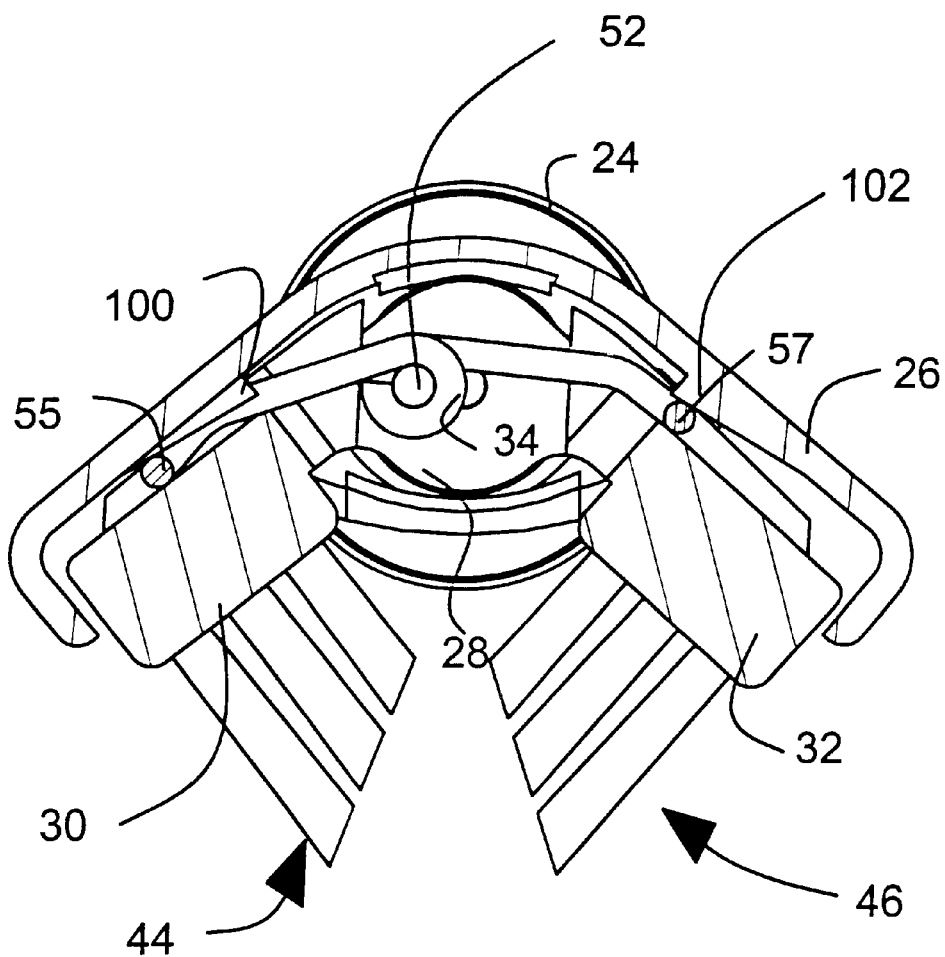
FIG. 11 is a view similar to FIG. 10, with the blocks having been rotated to their clockwise limit.

An inspection of FIGS. 9 through 11 will show that, when there is a reciprocating motion imparted to the link arms 54, 56, driving cam members 55, 57 will slide from the top towards the bottom, or from the bottom towards the top, of the respective wedge 100, 102. For example, FIG. 9 shows each of the driving cam members 55, 57 in a neutral position. That is to say, each is half-way up or half-way down its respective wedge 100, 102.

However, as the crank 52 is rotated 90° clockwise, as shown in FIG. 10, it is seen that the driving cam member 57 has moved to the bottom of the wedge 102, and the driving cam member has moved to the top of the wedge 100. This has the effect of rotating the block 30 in a direction which is counter-clockwise away from the underside of the left portion of the fixed cover portion 26, as seen particularly in FIG. 10.

Likewise, when the crank 52 has rotated another 180°, as shown in FIG. 11, the driving cam member 55 has moved to the bottom of its respective wedge 100, and the driving cam member 57 has moved to the top of its respective wedge 102. This has the effective of rotating the block 32 in a direction clockwise away from the underside of the fixed cover member 26 at the right side thereof, as seen particularly in FIG. 11.

Of course, the blocks 30 and 32 are fixed one with respect to the other, so that as either of them rotates clockwise or counterclockwise, so does the other, thereby giving the oscillatory motion which is suggested in FIG. 4B.

It will also be seen that by varying the height of the blocks 30, 32, or the diameters of the driving cam members 55, 57, or the height and slope of the wedges 100, 102, the amount of oscillatory movement can be adjusted.

Typically, the amount, of oscillatory movement which is appropriate is in the range of 3° to 7°, with 4° to 5° being found to be particularly acceptable.

Figure 3:
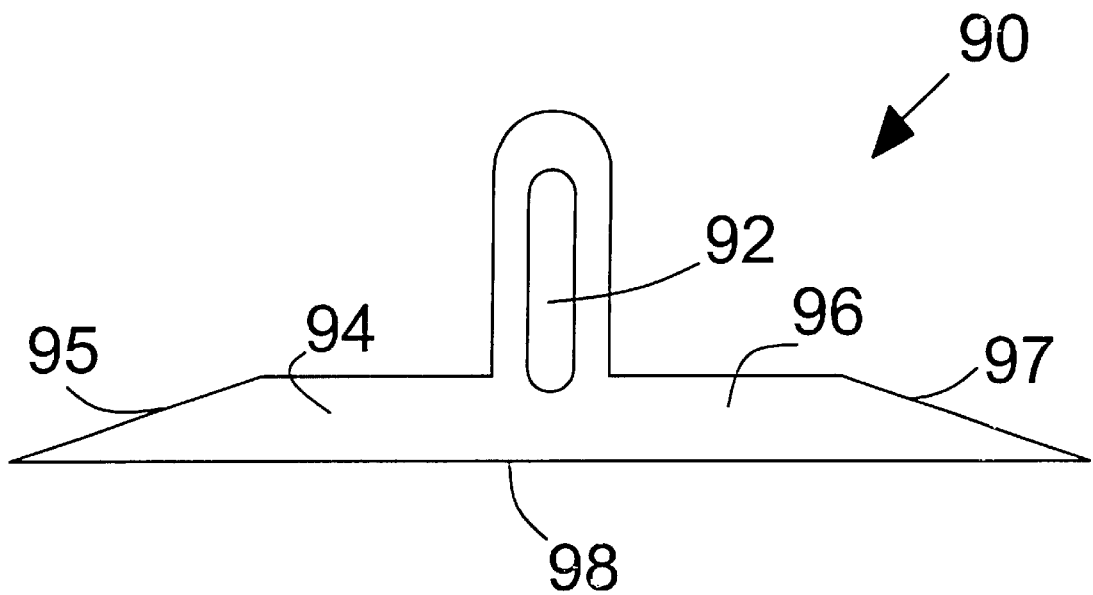
FIG. 3 shows a detail of an alternative shuttle block which may be used in the head portion of the toothbrush.

An alternative arrangement can be achieved by adopting the shuttle block 90 shown in FIG. 3 in place of the pair of link arms 54, 56. Here, the shuttle arm 90 is essentially T-shaped, having arms 94 and 96 with a substantially planar bottom surface 98. At the ends of arms 94, 96 there are downwardly and outwardly ramped portions 95, 97, respectively, in the upper surface of the arms 94, 96.

The crank 52 fits into the slot 92 and, because the ramped portions 95, 97 fit against the wedges 100, 102, rotation of the crank 52 will result in side-to-side motion of the shuttle block 90, with the crank 52 assuming similar positions relative to the longitudinal axis 34 of the stem 28 as are shown in FIGS. 9, 10, and 11.

The ramped portions 95, 97 slide in a sliding wedge action against the wedges 100, 102, respectively, The planar bottom surface 98 reacts against one or the other of the opposed blocks 30, 32, so as to impart the oscillatory movement of the pair of opposed bristle head portions 40, 42 in much the same manner as discussed previously.

It will be noted that the mass which is actually oscillated, in keeping with the present invention, is very low relative to prior art devices. The mass which is oscillated comprises only the drive shaft 36, the driving means 54, 56, or 90, and the stem 28 together with the bristle heads 40, 42 and bristle bundles 44, 46. Most prior art devices require that the entire head be oscillated, or at least a substantial portion thereof.

Moreover, it will be seen that, during operation of the toothbrush in keeping with the present invention, the fixed cover portion 26 has no movement whatsoever. This results in two advantages:

First, the bristle heads 40, 42 can be oscillated at higher rates—typically, 4,000 to 6,000 per minute, as opposed to the only 2,000 to 3,000 oscillations which were previously attainable. Second, a very comfortable mouth feel is achieved, because the only moving parts of the toothbrush are the bristle bundles 44, 46 acting against the teeth. The soft tissues of the mouth are not exposed to vibratory stimulation which might be transferred to the soft tissues from the oscillating dual head of the toothbrush—it having been found that such vibratory stimulation may be quite unpleasant.

Of course, since the mass which is oscillated is lower than in other prior art devices, a lower powered battery and motor can be employed, or at least the battery life can be extended.

A typical material from which the brush head portion 14, particularly the material of the blocks 30, 32 and stem 28 and the hollow shaft portion 24 together with the cover portion 26, is ABS. The shuttle block 90 might also be formed of ABS.

The drive shaft 36 is typically made from stainless steel, as is the pair of link arms 54, 56.

Figure 5:
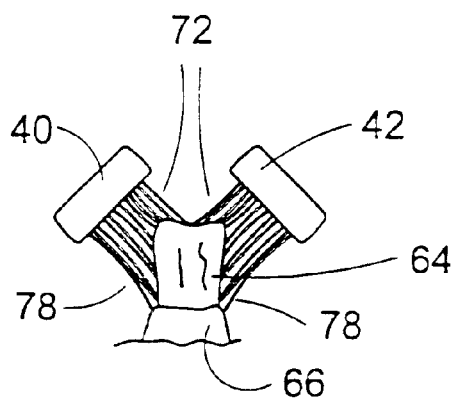
Figure 6:
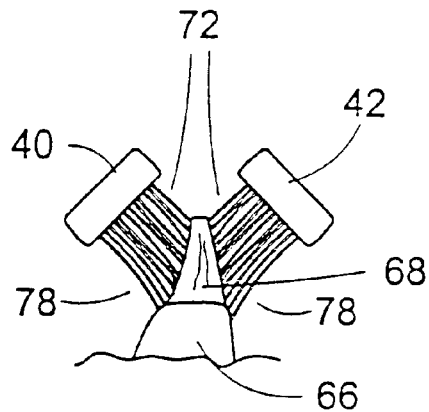

Finally, referring to FIGS. 5 and 6, the advantage of the present invention will become obvious. In FIG. 5, a typical molar 64 is shown together with its supporting gum structure 66. It is seen that the inner bristle bundles 72 on the respective bristle head portions 40 and 42 engage and will clean the occlusal surface of the tooth 64, whereas the remaining bristle bundles will engage and clean the buccal and lingual surfaces of the tooth 64. The oscillatory movement is, as noted above, only in the range of 3° to 7°, and at a rate of 4,000 to 6,000 oscillations per minute. Thus, the ends of the bristle bundles will be bent and will be constantly changing directions. They will, therefore, probe around the occlusal, buccal, and lingual surfaces of the tooth, and the probe will be effected with limited but effective chiselling action.

Indeed, it is believed that use of many typical prior art electric toothbrushes, particularly those which cause a sweeping motion either rotationally or longitudinally, particularly when combined with the use a typical abrasive dentifrice, actually causes thinning of the tooth enamel. Thus, the rapid but very short strokes of the toothbrush of the present invention are much less likely to cause enamel thinning or other damage to the teeth while, at the same time, providing a more efficient cleaning action due to the short stroke and the constantly changing direction of motion of the bristle ends.

The same conditions are noted in FIG. 6, where a typical front tooth 68 is shown, having its buccal and lingual surfaces cleaned, as well as its occlusal surface to the extent that such surface exists.

It is evident that there is no necessity for there to be any great amount of pressure applied by the user in pressing the bristles of the bristle head portions against the teeth.

It is to be particularly noted that a specific purpose of the present invention is to provide a brush head portion for an electric toothbrush, where the brush head portion may be adapted to fit power handles that are already available and in the market. Thus, no details of the power handle portion 12 have been provided, as such a power handle can be purchased, if necessary and if the particular design of the mating arrangement for the brush head portion 14 accommodates it, off the shelf. However, since the mass which is to be driven is considerably less than the mass of a vibrating brush head portion of prior art toothbrushes, it is possible that the electric motor in the power handle will sense a lighter load and will, in fact, rotate faster. Thus, an oscillatory motion of the dual brush head of the present invention may be at a higher oscillatory rate than the rate of vibration of a ordinary electric toothbrush being driven from the same power handle.

Still further, some power handles may exist or can be developed which will provide a reciprocating motion. If so, then it is only necessary for the end portion of the brush head—the stem and opposed bristle head portions—to be fitted to an oscillatory drive. In that case, the fitment of the head portion to a power handle portion may come at parting line 25, noted in FIG. 2.

There has been described an electric toothbrush which exhibits obvious advantages over prior art electric toothbrushes, and which particularly provides an apparatus which improves upon the highly promoted Bass Technique for brushing the teeth. The precise materials of the bristles and their manufacture are well known to the industry, as is the provision of a suitable power handle portion having an appropriate electric motor and linear reciprocating motion drive shaft. However, their application to an electric toothbrush in keeping with the present invention falls within the scope of the accompanying claims.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

What is claimed is:

1. A brush head portion for an electric toothbrush, said brush head portion being adapted to be removably connected to a power handle portion, including a driving mechanism located therein;

said brush head portion being removably attachable at a first end thereof to a power handle portion;

said brush head portion comprising a pair of opposed bristle head portions arranged so as to present two groups of opposed bundles of bristles disposed substantially perpendicularly each to the other, each of said groups of bundles of bristles on each respective bristle head portion comprising a plurality of rows and a plurality of columns of bristle bundles;

said brush head portion further comprising a longitudinal hollow shaft portion and a fixed cover portion at a second end thereof remote from said first end, said cover portion being shaped and dimensioned so as to overlie said pair of opposed bristle head portions;

said pair of opposed bristle head portions being mounted on a stem so as to form a pair of opposed blocks extending forwardly from said stem in a direction away from said first end of said brush head portion, said stem having a longitudinal axis, and said pair of opposed blocks being disposed at either side thereof;

a longitudinal drive shaft extending through said hollow shaft portion, and having a coupling at a first end adapted to receive rotational driving force from said driving mechanism;

said longitudinal drive shaft extending longitudinally through said stem along the longitudinal axis thereof, and having a crank formed at a second end remote from said first end;

drive means located between each of said pair of opposed blocks and the underside of a respective region of said fixed cover portion which overlies each respective one of said pair of opposed blocks, said drive means being mounted on said crank so as to have reciprocating motion imparted thereto as said crank is driven from said drive shaft; and a wedge formed on one of the underside of the fixed cover portion in the region overlying each respective one of said pair of opposed blocks, or on the top surface of each respective block;

whereby, when a reciprocating motion is imparted to said drive means by said crank, said drive means is moved from side-to-side so as to slide from the top towards the bottom of one of said wedges and from the bottom towards the top of the other of said wedges, and so as to thereby impart an oscillatory movement to said pair of opposed bristle head portions.

2. The brush head portion for an electric toothbrush, as claimed in claim 1, wherein a wedge is formed on the top surface of each respective block;

wherein said drive means comprises a pair of link arms, each having a driving cam member formed at the end thereof and extending in a direction parallel to the longitudinal axis-of said stem; and wherein each driving cam member is arranged to slide in camming relation with respect to the respective one of said blocks and the respective one of said wedges, and thereby so as to impart said oscillatory movement of said pair of opposed bristle head portions about the longitudinal axis of the stem portion thereof.

3. The brush head portion for an electric toothbrush, as claimed in claim 2, wherein the material of said brush head portion is ABS, and the material of said drive shaft and said driving means is stainless steel.

4. The brush head portion for an electric toothbrush, as claimed in claim 1, wherein said wedges are formed on the underside of the respective region of said fixed cover portion, and said drive means comprises a pair of link arms, each having a driving cam member formed at the end thereof and extending in a direction parallel to the longitudinal axis of said stem;

wherein the top surface of each of said blocks has a channel formed therein so as to receive and retain a respective one of said driving cam members; and wherein each driving cam member is captured in its respective channel between the respective block and wedge, so as to slide in camming relation therebetween and thereby so as to impart said oscillatory movement of said pair of opposed bristle head portions about the longitudinal axis of the stem portion thereof.

5. The brush head portion for an electric toothbrush, as claimed in claim 4, wherein the material of said brush head portion is ABS, and the material of said drive shaft and said driving means is stainless steel.

6. The brush head portion for an electric toothbrush, as claimed in claim 1, wherein said wedges are formed on the underside of the respective regions of said fixed cover portion, and said drive means comprises a T-shaped shuttle block having a substantially planar bottom surface and downwardly and outwardly ramped portions in the upper surface thereof;

said ramped portions being dimensioned and located so as to interact with said wedges as reciprocating motion is imparted to said shuttle block so as to cause a sliding wedge action between said wedges and said ramped portions, whereby the planar bottom surface of said shuttle block reacts against one or the other of said opposed blocks so as to thereby impart said oscillatory movement of said pair of opposed bristle head portions about the longitudinal axis of the stem portion thereof.

7. The brush head portion for an electric toothbrush, as claimed in claim 6, wherein the material of said brush head portion and said drive means is ABS, and the material of said drive shaft is stainless steel.

8. The brush head portion for an electric toothbrush, as claimed in claim 7, wherein the amount of oscillatory motion is in the range of 4° to 5°.

9. The brush head portion for an electric toothbrush, as claimed in claim 1, wherein the rows of bristle bundles of each of said groups of bundles of bristles are aligned parallel to the longitudinal axis of said brush head portion, and the columns of bristle bundles are aligned perpendicular to the longitudinal axis of said brush head portion; and wherein the bristles in each bundle in each row of bristle bundles on each bristle head portion are substantially equal in length, where the length of the bristles in the respective row of bristle bundles on each bristle head portion which is closest to the longitudinal axis of said brush head portion is shorter than the length of the bristles in the respective row of bristle bundles on each bristle head portion which is furthest away from the longitudinal axis of said brush head portion, and wherein the lengths of the bristles in each respective row of bristle bundles on each bristle head portion are progressively longer in each row of bristle bundles which is further away from the longitudinal axis of said brush head portion than an adjacent row of bristle bundles which is closer to the longitudinal axis of said brush head portion.

10. The brush head portion for an electric toothbrush, as claimed in claim 1, wherein the amount of oscillatory motion by said opposed bristle head portions of said brush head portion about the longitudinal axis of said stem is in the range of 3° to 7°.

11. The brush head portion for an electric toothbrush, as claimed in claim 1, wherein the rate of oscillatory movement by said opposed bristle head portions of said brush head portion about the longitudinal axis of said stem is in the range of 4,000 to 6,000 oscillations per minute.

12. An electric toothbrush comprising a power handle and a brush head portion;

said power handle portion being adapted to provide a housing for an electric motor and for a driving mechanism located at a first end of said power handle portion;

said driving mechanism being powered by said electric motor;

said brush head portion being removably attachable at a first end thereof to said first end of said power handle portion;

said brash head portion comprising a pair of opposed bristle head portions arranged so as to present two groups of opposed bundles of bristles disposed substantially perpendicularly each to the other, each of said groups of bundles of bristles on each respective bristle head portion comprising a plurality of rows and a plurality of columns of bristle bundles;

said brush head portion further comprising a longitudinal hollow shaft portion and a fixed cover portion at a second end thereof remote from said first end, said cover portion being shaped and dimensioned so as to overlie said pair of opposed bristle head portions;

said pair of opposed bristle head portions being mounted on a stem so as to form a pair of opposed blocks extending forwardly from said stem in a direction away from said first end of said brush head portion, said stem having a longitudinal axis, and said pair of opposed blocks being disposed at either side thereof;

a longitudinal drive shaft extending through said hollow shaft portion, and having a coupling at a first end adapted to receive rotational driving force from said driving mechanism;

said longitudinal drive shaft extending longitudinally through said stem along the longitudinal axis thereof, and having a crank formed at a second end remote from said first end;

drive means located between each of said pair of opposed blocks and the underside of a respective region of said fixed cover portion which overlies each respective one of said pair of opposed blocks, said drive means being mounted on said crank so as to have reciprocating motion imparted thereto as said crank is driven from said drive shaft; and a wedge formed on one of the underside of the fixed cover portion in the region overlying each respective one of said pair of opposed blocks, or on the top surface of each respective block;

whereby, when a reciprocating motion is imparted to said drive means by said crank, said drive means is moved from side-to-side so as to slide from the top towards the bottom of one of said wedges and from the bottom towards the top of the other of said wedges, and so as to thereby impart an oscillatory movement to said pair of opposed bristle head portions.

13. The electric toothbrush of claim 12, wherein a wedge is formed on the top surface of each respective block;

wherein said drive means comprises a pair of link arms, each having a driving cam member formed at the end thereof and extending in a direction parallel to the longitudinal axis of said stem; and wherein each driving cam member is arranged to slide in camming relation with respect to the respective one of said blocks and the respective one of said wedges, and thereby so as to impart said oscillatory movement of said pair of opposed bristle head portions about the longitudinal axis of the stem portion thereof.

14. The electric toothbrush of claim 12, wherein said wedges are formed on the underside of the respective region of said fixed cover portion, and said drive means comprises a pair of link arms, each having a driving cam member formed at the end thereof and extending in a direction parallel to the longitudinal axis of said stem;

wherein the top surface of each of said blocks has a channel formed therein so as to receive and retain a respective one of said driving cam members; and wherein each driving cam member is captured in its respective channel between the respective block and wedge, so as to slide in camming relation therebetween and thereby so as to impart said oscillatory movement of said pair of opposed bristle head portions about the longitudinal axis of the stem portion thereof.

15. The electric toothbrush of claim 12, wherein said wedges are formed on the underside of the respective regions of said fixed cover portion, and said drive means comprises a T-shaped shuttle block having a substantially planar bottom surface and downwardly and outwardly ramped portions in the upper surface thereof;

said ramped portions being dimensioned and located so as to interact with said wedges as reciprocating motion is imparted to said shuttle block so as to cause a sliding wedge action between said wedges and said ramped portions, whereby the planar bottom surface of said shuttle block reacts against one or the other of said opposed blocks so as to thereby impart said oscillatory movement of said pair of opposed bristle head portions about the longitudinal axis of the stem portion thereof.

* * * * *